United States Patent [19]

Bonifacio

[11] Patent Number: 4,462,987

[45] Date of Patent: Jul. 31, 1984

[54] PROCESS AND COMPOSITION FOR TREATING TUMORS IN MICE

[76] Inventor: Liborio Bonifacio, Via Q. Sella 5, Agropoli, Italy

[21] Appl. No.: 357,694

[22] Filed: Mar. 12, 1982

Related U.S. Application Data

[63] Continuation-in-part of Ser. No. 195,510, Oct. 10, 1980, abandoned.

[30] Foreign Application Priority Data

Oct. 11, 1979 [CH] Switzerland .................. 9195/79

[51] Int. Cl.³ .................. A61K 35/32; A61K 35/12; A61K 35/56
[52] U.S. Cl. .................. 424/99; 424/95
[58] Field of Search .................. 424/99, 95

[56] References Cited

FOREIGN PATENT DOCUMENTS 2161779  7/1973  France .
1326928  8/1973  United Kingdom .

OTHER PUBLICATIONS

Biological Abstracts, vol. 65, 15/4/78, abstract 45712, W. L. McGuire et al. "Progress in Cancer Research and Therapy", vol. 4, Progesterone Receptors in Normal and Neoplastic Tissues.
Chemical Abstracts 48:8935c (1954).
Spencer, Cancer Research, Part 2, vol. 25, No. 4, May 1965, p. 839, (No. 2838).

Primary Examiner—Jerome D. Goldberg
Attorney, Agent, or Firm—Young & Thompson

[57] ABSTRACT

This invention relates to a process and composition for preventing the onset or retarding the growth of tumors in mice employing extracts from feces and urine of male or female goats.

9 Claims, 7 Drawing Figures

PROCESS AND COMPOSITION FOR TREATING TUMORS IN MICE

This application is a continuation-in-part of Ser. No. 195,510, filed Oct. 10, 1980, and now abandoned.

The present invention relates to a process and composition for preventing the onset or retarding the growth of tumors in mice.

It has been discovered that extracts from the feces and urine of male or female goats are effective for the prevention and retardation of growth of various tumors in mice.

The process of extraction consists in soaking the feces and urine of the same animal in a quantity of water, preferably twice distilled, filtering the material thus produced by normal filtration, and then filtering the material in a sterilizing filter for example of the "millipore" type.

The process of preparation of the extract from the male or female goat is as follows:

1. The feces of the male or female goat are mixed with several parts of urine of the same animal, with approximately ½ part by volume of twice distilled water.
2. This mixture is allowed to stand for approximately 48 hours.
3. The mixture is then filtered, first with normal filter paper and then with a sterilizing filter known as "millipore", thereby obtaining a liquid dark straw-yellow substance which is the completed extract.

In greater detail, 100-500 cc of feces is mixed with 100 cc urine, in admixture with twice distilled water in the amount of 33.3-200 cc. The preferred ratio is 100 cc urine plus 500 cc (approximately 500 g) feces plus 200 cc twice distilled water, which is then allowed to stand and then filtered as described above.

The resultant filtrate is administered by inoculation to mice in the amount of 0.20-3.5 microliter/g of body weight, preferably 1 to 2 microliter/g of body weight.

The mice used in the above and following tests were inbred with the Balb/c strain. As is well known, this strain is characterized by a high occurrence of spontaneous tumors of the mammary gland. Spontaneously occurring carcinomas, as well as those obtained through transplantation, grow at a phenomenal rate, causing the death of the mice after an average period of 50 days following onset.

In the accompanying drawings

Figure 4:
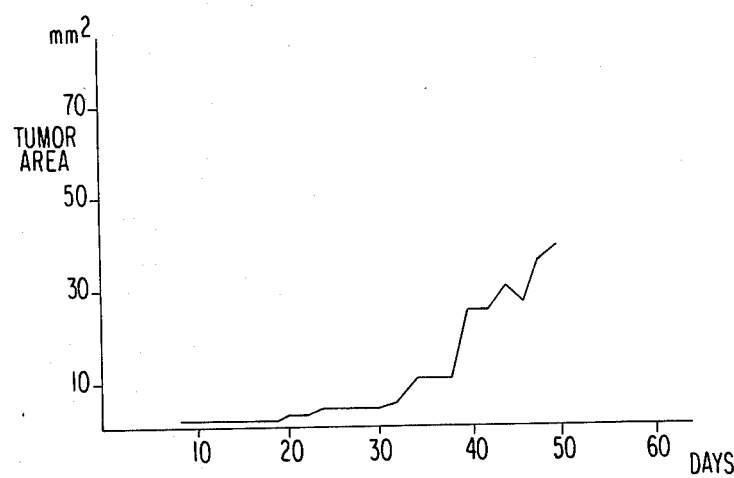
FIG. 4 is a graph of tumor size versus time, for a group of mice in which treatment is begun only after an implanted tumor has reached an area of 1 $mm^2$.
Figure 5:
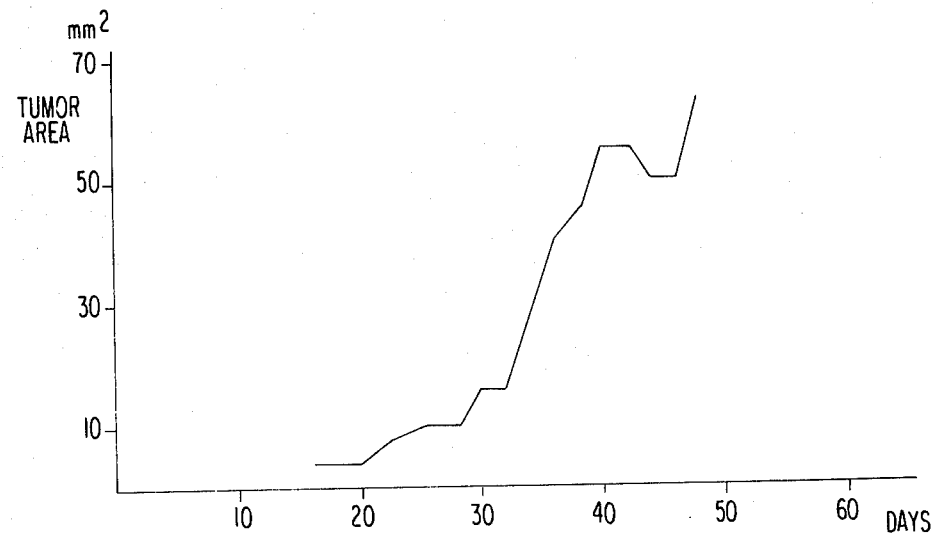
Figure 6:
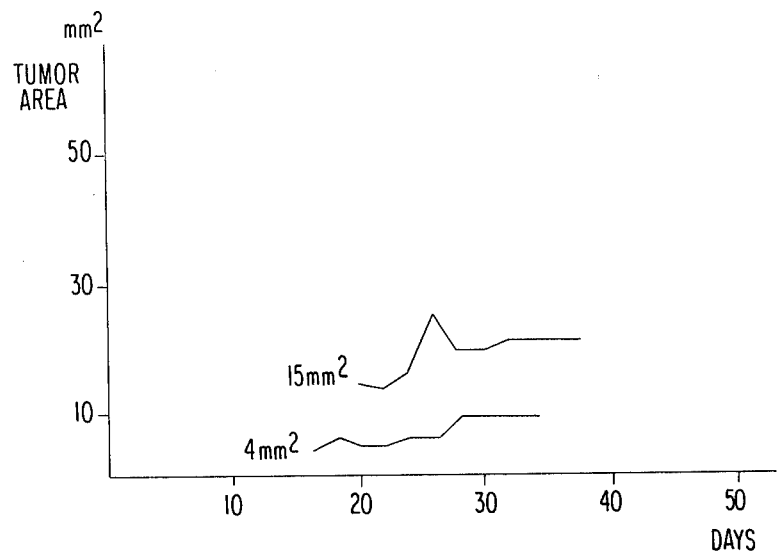
Figure 7:
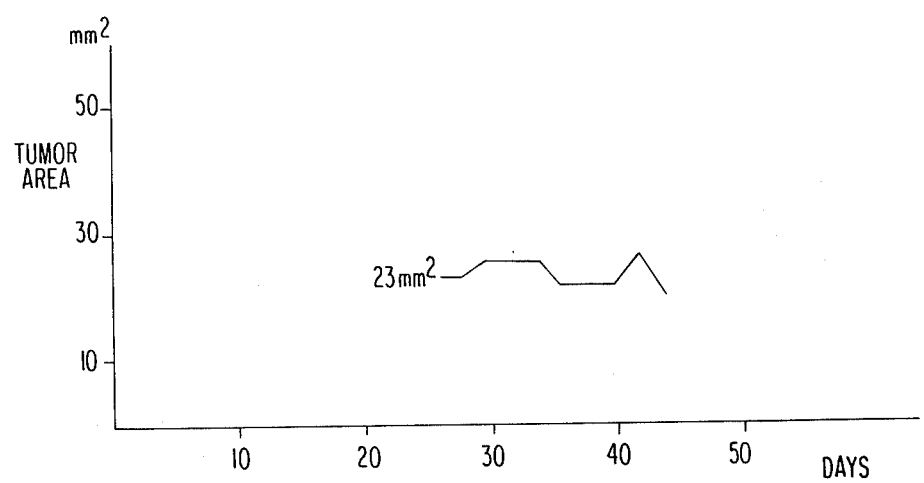

FIG. 5 is a view similar to FIG. 4, but in which treatment was begun after the tumor had reached an area of 4 $mm^2$; and FIGS. 6 and 7 are graphs of the area of transplanted carcinomas whose size at the onset of treatment is 4 and 15 $mm^2$ (FIG. 6) and 23 $mm^2$ (FIG. 7), when treated with the present invention plus hydrocortisone.

Figure 1:
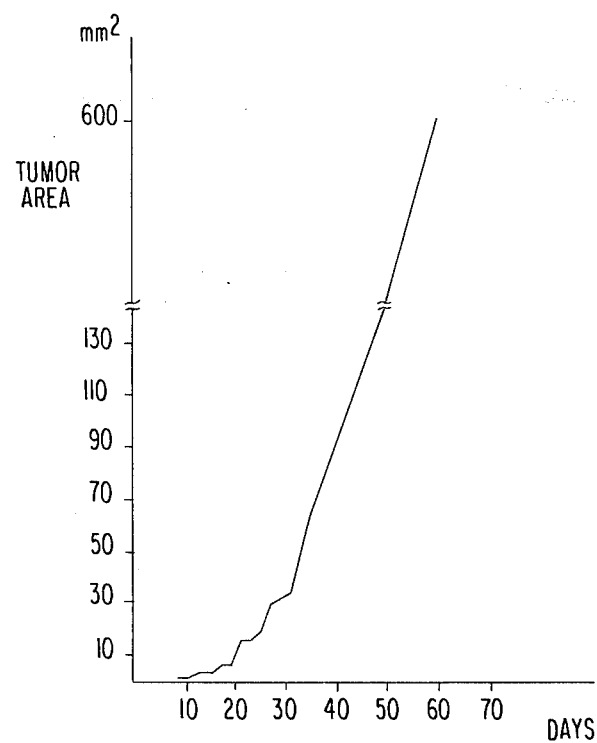
FIG. 1 is a graph of tumor area versus days after implantation of a transplanted tumor, performed on control mice not treated according to the present invention.

As can be seen from FIG. 1, whose values are average measurements performed on a group of control mice, the increase in area of the neoplasm proper, given in $mm^2$, is very rapid, increasing five-fold after seven days and reaching 50 $mm^2$ after 26 days after the appearance of the neoplasm, and causing the death of the mice after 51 days after said appearance, with a tumor mass equivalent to 600 $mm^2$.

In each case, the transplanted or infiltrating carcinoma is of the mammary gland, maintained by means of iso-transplants.

As to whether the preparation of Example 1 exercises a preventive action against the growth of the tumor, 100 mice of both sexes between the ages of 18 and 24 days were pretreated with the material of Example 1, whereafter a neoplasm was transplanted into each. In 20% of the cases, no tumor appeared at all. In 12% of the cases, a tumor appeared after 30 days; and in the remaining 68% of the cases a tumor appeared 15 days after transplant (FIG. 2).

By contrast, in a group of control mice of the same Balb/c strain, the transplanted neoplasm grew in 100% of the cases and always appeared between the 7th and 10th day, and no later (FIG. 1).

In the 12% of the cases where the neoplasm described above appeared after 30 days following transplant, the tumor (FIG. 2) doubled in size in 54 days. By contrast, in the untreated controls, this occurred within 24 hours. In such cases, the transplanted neoplasm treated according to the present invention retained, to the end of the experiment (100 days) the same area of 2 $mm^2$, as is shown by the lower curve in FIG. 2.

Figure 2:
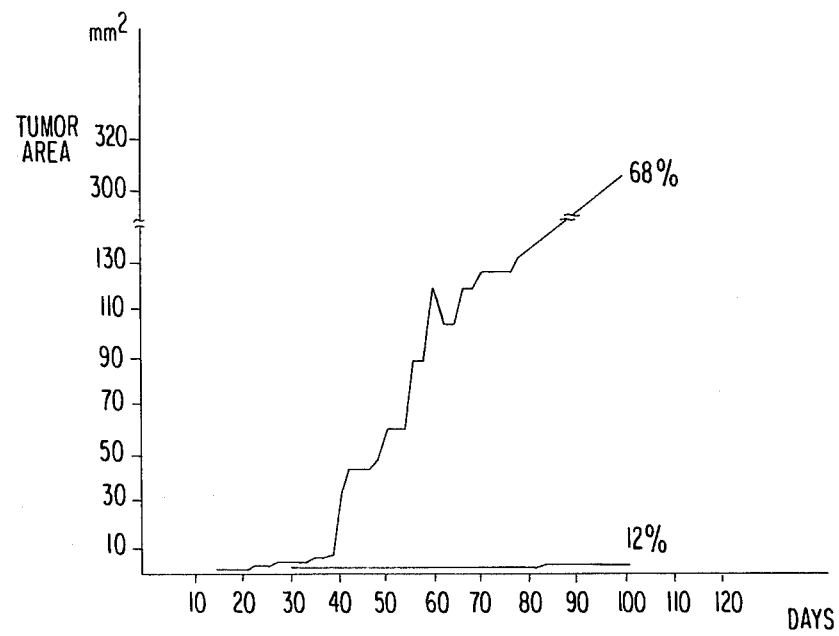
FIG. 2 is a graph of the growth rate of carcinomas appearing after 15 days in a group of mice treated according to the present invention.

With respect to the 68% of the cases in which the carcinoma appeared after 15 days, the neoplasm grew five-fold in 24 days, as shown in FIG. 2. By contrast, in the controls, this five-fold growth occurred after 7 days, reaching 50 $mm^2$ in 26 days after appearance, as distinguished from 34 days after appearance in the treated mice. In the treated mice, after 51 days after appearance, the neoplasm was still 102 $mm^2$ in size; whereas death ensued in the controls. The treated mice were alive at the end of the experimental period (100 days).

In the tests recorded in FIGS. 1-7, the preparation was administered intramuscularly, which is preferable to subcutaneous or intraperitoneal inoculation.

As to dilution, it has been found that the concentrated preparation described in FIG. 1, namely, the filtrate of 100 cc urine plus 500 cc feces plus 200 cc twice-distilled water, is best used as such, although, as shown further in Example 1, dilution is acceptable.

Based on the undiluted concentrate, it has been found that there is an optimum range of administration. At dosage levels of 0.5 to 3.5 microliters/g of body weight, the retardation of growth of the neoplasm was discernible but not marked. Above 3.5 microliter/g of body weight, no improvement was noted; and so these higher concentrations are believed to be merely wasteful.

But optimum results were obtained at about 1 to 2 microliter/g of body weight.

As to the treatment regimen, 100 mice of an average body weight of 22 g each, were injected with either 25 microliters or 50 microliters of the concentrate intramusucularly, in a treatment cycle shown in Tables 1 and 2 below.

TABLE 1

| Days | 1 | 2 | 3 | 4 | 5 | 6 | 7 | 8 | 9 | 10 | 11 | 12 | 13 |
|---|---|---|---|---|---|---|---|---|---|---|---|---|---|
| μl | 25 | 25 | 25 | None | 50 | 50 | 50 | None | None | 25 | 25 | 25 | None |

TABLE 2

| Days | 1 | 2 | 3 | 4 | 5 | 6 | 7 | 8-13 | 14 | 15-23 | 24 | 25-40 | 41 |
|---|---|---|---|---|---|---|---|---|---|---|---|---|---|
| μl | 25 | 25 | 25 | None | 50 | 50 | 50 | None | 25 | None | 25 | None | 25 |

Figure 3:
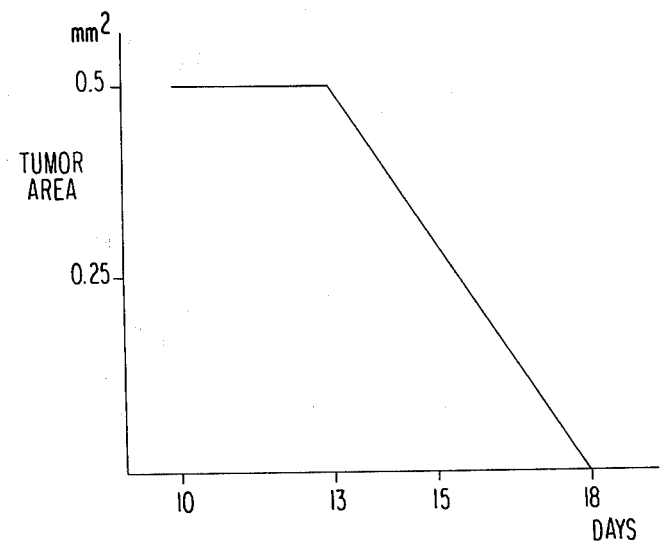
FIG. 3 is a graph of carcinoma size versus time, for a group of mice in which an untreated carcinoma has reached a predetermined size and then is treated according to the present invention.

To test the effect of the preparation according to the present invention on existing tumors, neoplasms were implanted as above in a group of test mice; and when the neoplasm reached an area of 0.25 mm$^2$, then the mice were treated as above. The results are shown in FIG. 3, in which it will be seen that the neoplasms begin to decrease in area after 13 days, were reduced by half after 15 days and in 78% of the cases had disappeared completely by the 18th day. Thereafter, maintenance doses were given at increasing intervals of time (Table 2). By the end of the experimental period (100 days) no recurrence was noted in any of the mice from which the neoplasm had completely disappeared.

In the remaining 22% of the cases, the neoplasm grew, but much more slowly than in the controls.

The concentrate was administered to 100 other mice as soon as the size of the transplanted tumor reached 1 mm$^2$. In this case, there was no total regression; however, growth was greatly retarded relative to the controls. As is seen from FIG. 4, the tumors retained their initial size of 1 mm$^2$ for 18 days, after appearance, then doubled in size and continued to grow very slowly.

Another 100 mice were treated with the concentrate as soon as the size of the transplanted neoplasm had reached 4 mm$^2$. As is seen from FIG. 5, in this case, the transplanted neoplasm grew more slowly than in the controls, although the mass increased more rapidly, in terms of mm$^2$/day, than when the treatment was started when the tumors were smaller.

Finally, another group of 100 implanted mice were treated when the tumoral mass was of an area of 9 mm$^2$. Although in this group the neoplasm grew more slowly than in the controls, nevertheless, the growth rate in mm$^2$/day was higher than in the illustrated cases in which treatment was started when the tumor was smaller.

From the above, it will be evident that the present invention exerts an anti-tumor action which is very marked if the therapy is applied to neoplasms that are not yet in a terminal state and brings about in fact a high rate of total remission (e.g. 78%) of the tumoral mass when started sufficiently early, this remission being apparently permanent. On the other hand, the total disappearance of the tumor is unlikely when the mass has reached a considerable size, although even then its growth is retarded.

The following further illustrative examples are given:

EXAMPLE 1

Ten female mice, aged 30 days, were inoculated peritoneally each day for 14 consecutive days with material prepared with the preferred proportions as above, diluted tenfold with 0.9% NaCl. The material was prepared from male goat and the amount inoculated each day was 0.2 ml. On the 15th day, each mouse was transplanted with a carcinoma which infiltrates the breast, which originates spontaneously and which is maintained with the same histological characteristics by iso-transplantation of fragments of about 1 mm, effected in the upper right thoracic region. Thereafter, the same treatment was continued, but on alternate days. The typical pinhead configuration was palpated, which is a sign of the appearance and taking root of the transplanted carcinoma, after 15 days in eight of the ten mice; while in two of them, nothing was felt.

This is in contrast to earlier experience, that such carcinoma develops after six to seven days from transplant and grows very rapidly, which brings about the appearance of metastasis in the lungs. In fact, in untreated control mice, subjected to the same transplant, the transplant took in 100% of the cases in six or seven days from the time of transplant. The pinheads in the control group doubled in volume six days after the first appearance of the pinheads and this speed of growth was maintained until the control mice died in about two months.

EXAMPLE 2

Ten male mice, 30 days old, were pretreated for 14 days in the same manner as Example 1. Transplant was performed in the same manner as Example 1 on the 15th day; and thereafter the mice were injected intramuscularly with 0.05 cc of undiluted preparation from male goat, administered on alternate days. 18 days from transplant, only two mice showed the pinhead and in the other either there was nothing.

EXAMPLE 3

Five female mice, age 30 days, were pretreated for 11 consecutive days with 0.5 cc of the tenfold-diluted material of Example 1, inoculated intraperitoneally. On the 12th day, transplant was performed as in EXAMPLE 1. The carcinomas were still in the pinhead shape after 16 days, and maintained the same size for six further days, after which they slightly increased in size.

EXAMPLE 4

Five female mice were treated as in Example 3, the difference being that 0.4 cc was inoculated instead of 0.5 cc. The tumor was palpable in all of the mice after 10 days.

EXAMPLE 5

Five male mice were treated as in Example 3. The quantity of tenfold-diluted material was 0.2 cc. Carcinoma appeared in 14 days and then, proportional to the length of time from the day of transplant, retained very small dimensions. The carcinomas were comparable to a grain of rice.

EXAMPLE 6

Five male mice were treated with 0.1 cc of preparation, administered in the same manner and with the same timing as in Example 3. The pinhead was palpable after 10 days.

EXAMPLE 7

Ten male mice, aged 30 days, were transplanted as in Example 1, and then, every 24 hours, were injected intraperitoneally with 0.2 cc of preparation as in Example 1. The carcinoma appeared after 10 days.

EXAMPLE 8

Ten female mice were injected intraperitoneally with 0.5 cc of preparation as in Example 1. Seven days after transplant, during which seven days the preparation had been administered on alternate days, the carcinoma was palpable as a pinhead. After one month of such treatment, the tumor was of reduced dimensions particularly with respect to that of the control mice described above.

The present invention is not limited to the treatment of implanted tumors but rather is useful also in the treatment of spontaneous cancer of the mammary gland in mice. In such cases, the tumor appears almost simultaneously with metastases in the homolateral or contralateral breasts. Thus, the prognosis for treatment of a spontaneous tumor is obviously less favorable than that of an early transplanted tumor, simply because the tumor is evident only when it has reached relatively large size.

In test mice in which the tumors arose spontaneously, which were treated with the present invention, there was a marked extirpation of the carcinoma with elimination of neoplastic cells which, in part, had lost their typical malignant traits. Furthermore, the onset of healing occurred within a few hours; and where hemorraging had occurred, this disappeared. In many cases, there was an appreciable reduction in the tumor mass, but it was found to be only temporary. In all cases of spontaneous tumor treated to date, there has been observed a notable lengthening of the survival time in the mice in comparison with the non-treated controls, and a reduction of a display of pain.

It has also been found that the growth of tumors in mice is further retarded by use of the preparation according to the present invention in combination with hydrocortisone. As pointed out above, the preparation alone does not bring about the total regression of the neoplasm when it has reached a very advanced stage of development. The hydrocortisone is administered by inoculation in admixture with the concentrate previously described, in an amount at least about 1 microliter/g of body weight, up to about 4 microliters/g of body weight, after which further hydrocortisone is merely wasteful. The preferred administration level is about 1 microliter/g of body weight of the mouse.

The results of conjoint administration of the concentrate plus hydrocortisone (1 microliter/g of body weight) are shown in FIGS. 6 and 7, on tumoral masses that have attained 4 and 15 $mm^2$ areas (FIG. 6) and 23 $mm^2$ areas (FIG. 7). As will be seen, the growth of the neoplasms has been substantially completely stopped but they remain at the same size. This is in contrast to the results shown in connection with the concentrate alone, in which tumors of such size continue to grow although treated with the concentrate alone.

It has also been discovered that marked regression of spontaneous breast tumors in mice can be achieved, if the concentrate described above is conjointly administered in inoculation in admixture with sodium dextran sulphate. The sodium dextran sulphate should be administered in an amount of 15 to 25 micrograms/g of body weight, preferably about 25 micrograms/g of body weight of the mouse.

What is claimed is:

1. A method for retarding the growth of carcinomas and tumors of the epithelial tissues, sarcomas and tumors of the connective tissue, including leukemia and carcinomas of the prostate, in mice, comprising administering to a tumorous mouse by inoculation an antitumor effective amount of a solution of the excrement of a goat, in which said solution is the filtrate of 33.3–200 parts of water, 100–500 parts of goat feces and 100 parts of goat urine.

2. A method as claimed in claim 1, in which said solution is administered in an amount between 0.20 and 3.5 micro liter/g of body weight.

3. A method as claimed in claim 2, in which said quantity is about 1 to 2 microliter/g of body weight.

4. A method as claimed in claim 1, in which said solution is administered in admixture with hydrocortisone in an amount about 1 to 4 microliter/g of body weight.

5. A method as claimed in claim 1, in which said solution is administered in admixture with sodium dextran sulphate in an amount about 15 to 25 mg/kg of body weight.

6. A composition for retarding the growth of carcinomas and tumors of the epithelial tissues, sarcomas and tumors of the connective tissue, including leukemia and carcinomas of the prostate, in mice, comprising a filtrate of a mixture of 33.3–200 parts water, 100–500 parts of goat feces and 100 parts of goat urine.

7. A composition as claimed in claim 6, which is the filtrate of a mixture of about 100 parts goat urine, 500 parts goat feces and 200 parts water.

8. A composition as claimed in claim 6, in admixture with about 0.5 to 4 parts by volume of hydrocortisone per part by volume of said filtrate.

9. A composition as claimed in claim 6, in admixture with 7 to 250 parts by weight of sodium dextran sulphate per part by weight of filtrate.

* * * * *